(12) United States Patent
Hoeg et al.

(10) Patent No.: US 7,427,263 B2
(45) Date of Patent: Sep. 23, 2008

(54) METHOD AND INTERFACE FOR OPERATING A VARIABLE DIRECTION OF VIEW ENDOSCOPE

(75) Inventors: Hans David Hoeg, Arcadia, CA (US); Nathan Jon Schara, Pasadena, CA (US); Eric Lawrence Hale, Altadena, CA (US)

(73) Assignee: Karl Storz Development Corp., Goleta, CA (US)

( * ) Notice: Subject to any disclaimer, the term of this patent is extended or adjusted under 35 U.S.C. 154(b) by 563 days.

(21) Appl. No.: 11/052,180

(22) Filed: Feb. 7, 2005

(65) Prior Publication Data

US 2005/0197535 A1   Sep. 8, 2005

Related U.S. Application Data

(60) Provisional application No. 60/549,838, filed on Mar. 3, 2004.

(51) Int. Cl.
*A61B 1/00* (2006.01)
(52) U.S. Cl. .................... 600/173; 600/118
(58) Field of Classification Search .......... 600/173, 600/160, 118
See application file for complete search history.

(56) References Cited

U.S. PATENT DOCUMENTS

| 3,856,000 | A | 12/1974 | Chikama | |
|---|---|---|---|---|
| 4,697,577 | A | 10/1987 | Forkner | |
| 5,313,306 | A | 5/1994 | Kuban et al. | |
| 5,575,754 | A * | 11/1996 | Konomura | 600/117 |
| 5,762,603 | A | 6/1998 | Thompson | |
| 5,800,341 | A | 9/1998 | McKenna et al. | |
| 6,371,909 | B1 | 4/2002 | Hoeg et al. | |
| 6,500,115 | B2 | 12/2002 | Krattiger et al. | |
| 6,560,013 | B1 | 5/2003 | Ramsbottom | |
| 6,626,828 | B2 * | 9/2003 | Dohi et al. | 600/173 |
| 6,638,216 | B1 * | 10/2003 | Durell | 600/173 |
| 6,663,559 | B2 | 12/2003 | Hale et al. | |
| 7,052,455 | B2 * | 5/2006 | Hale et al. | 600/118 |
| 7,175,593 | B2 * | 2/2007 | Durell | 600/173 |

* cited by examiner

*Primary Examiner*—John P Leubecker
(74) *Attorney, Agent, or Firm*—St. Onge Steward Johnston & Reens LLC

(57) ABSTRACT

A method and system are provided for configuring a variable direction of view endoscope generally comprising a graphical user interface and an endoscope having a view controlling device for moving the view vector between predefined, discrete view vector positions. The graphical user interface displays a set of these view vector positions, and the view vector is moved from one of these positions directly to another in response to a command from a user via the graphical user interface.

20 Claims, 5 Drawing Sheets

0°

30°

70°

120°

*Prior Art*

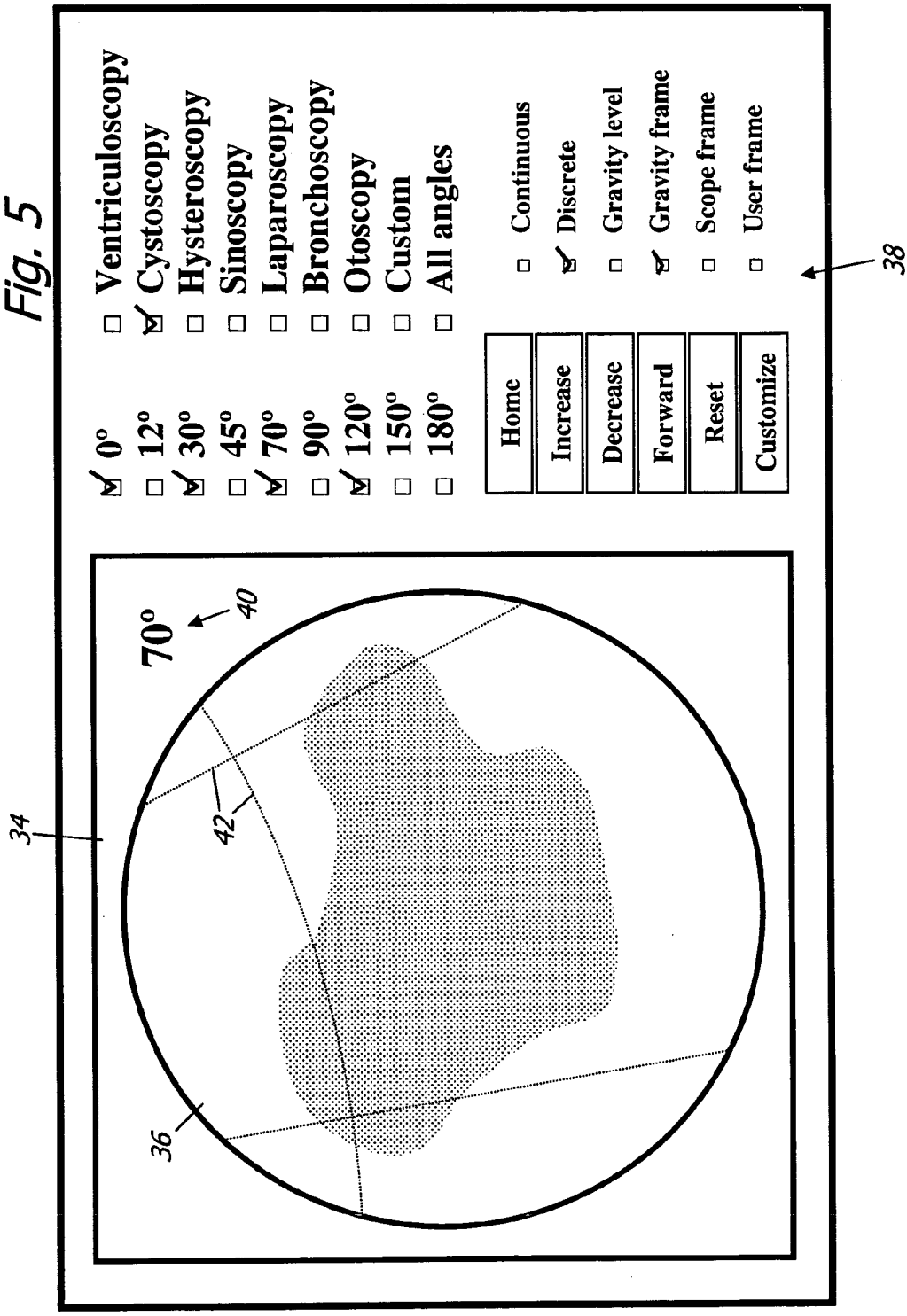

METHOD AND INTERFACE FOR OPERATING A VARIABLE DIRECTION OF VIEW ENDOSCOPE

CROSS-REFERENCE TO RELATED APPLICATIONS

This application claims the benefit of U.S. provisional application Ser. No. 60/549838 filed on Mar. 3, 2004, entitled "Method and interface for operating a variable direction of view endoscope", the contents of which are incorporated herein by reference.

FIELD OF THE INVENTION

The present invention relates to endoscopes and specifically to the operation of variable direction of view endoscopes.

BACKGROUND OF THE INVENTION

Traditionally rigid endoscopes have a fixed viewing direction. Depending on the endoscope, the viewing direction can be either straight forward along the longitudinal axis of the scope, or it can be set at an angle to the longitudinal axis. A variety of off-angles are available depending on the application. For example, in sinoscopy typical scope angles can be 0, 30, 45, 70, and 90, while in cystoscopy the angles are typically 0, 30, 70, and 120. The endoscopist needs this range of angles in order to maximize the visual coverage of an internal structure. With only a straight forward viewing scope, the viewing range is severely limited. In large cavities, such as the abdomen, the operator can compensate for a fixed forward viewing angle by changing the entry angle of the laparoscope, and can thus with skilled manipulation increase the viewing range somewhat. However, in many cases, such as neuroendoscopy, sinoscopy, or otoscopy, the endoscope shaft is physically constrained or must remain largely stationary to avoid injuring the patient.

There are a number of drawbacks with using multiple endoscopes of different angles. Firstly, and most critically, inserting an off-angle endoscope can be dangerous because the operator can not see forward while the scope is being inserted. This problem is so severe that in neuroendoscopy for example, many surgeons will not use off-angle endoscopes because they are afraid of damaging delicate brain tissue. The result of this is regularly missed tumors growing outside the visual range. Similarly, in cystoscopy and certain types of laparoscopy, the surgeons are often concerned with using off-axis scopes for fear of injuring tissue ahead of or behind the viewing side of the scope. Secondly, each time a scope must be retracted and replaced with a scope of different a viewing angle, the operator can lose orientation and established visual reference points. Thirdly, repeated insertions and retractions are time consuming and annoying. Finally, the preparation, storage, and cleaning required for multiple endoscopes is impractical. There is also significant additional cost associated with having to supply multiple endoscopes for each procedure.

There have been a number of attempts to design variable direction of view endoscopes which can change their line of sight in situ and thus remove the need for multiple instruments. Examples of such devices are disclosed in U.S. Pat. No. 3,856,000 to Chikama, U.S. Pat. No. 6,371,909 to Hoeg, U.S. Pat. No. 6,560,013 to Ramsbottom, U.S. Pat. No. 4,697,577 to Forkner, U.S. Pat. No. 6,500,115 to Krattiger et al., and U.S. Pat. No. 5,762,603 to Thompson, which mechanically or electromechanically change the viewing direction, and in U.S. Pat. No. 5,313,306 to Kuban, and U.S. Pat. No. 5,800,341 to McKenna et al., which electronically change the viewing direction within a large captured field. These endoscopes can be disorienting and difficult to control. Hale et al. in U.S. Pat. No. 6,663,559 solve these control and orientation problems by computer-aided navigation. While effective, the advanced capabilities afforded by Hale et al. are not always necessary, especially when doing certain types of diagnoses. While the methods taught by Hale et al. appear to be the future direction of endoscopy, most surgeons for example, have been trained to use endoscopes with fixed viewing angles and are therefore sometimes reluctant to adopt new endoscopic viewing techniques. Specifically, many surgeons have come to rely on the specific viewpoints provided by fixed angle scopes. Rather than endoscopically navigating a cavity attempting to correlate the view with a preexisting knowledge of what the anatomy should look like, surgeons tend to associate a certain endoscopic viewing angle with a certain view and have developed mental links between viewing reference points and scope types. They have also become accustomed to correlating the position of structural features on the endoscope, such as the light post, with the orientation and direction of the endoscopic view. These established mental couplings between the endoscope configuration and the live image have become and important part of the endoscopic viewing process and are therefore difficult to reform.

Accordingly, the object of the present invention is to provide endoscopists with the advantages of traditional fixed-angle endoscopy while avoiding the disadvantages of using multiple instruments. Still further objects and advantages will become apparent from the ensuing description and drawings.

BRIEF SUMMARY OF THE INVENTION

In accordance with the present invention, a variable direction of view endoscope can be configured to allow rapid switching between discrete viewing directions.

BRIEF DESCRIPTION OF THE DRAWINGS

FIG. 5 shows a graphical user interface according to the present invention.

DETAILED DESCRIPTION OF THE INVENTION

The following detailed description illustrates the invention by way of example, not by way of limitation of the principles of the invention. This description will enable one skilled in the art to make and use the invention, and describes several embodiments, adaptations, variations, alternatives and uses of the invention, including what we presently believe is the best mode of carrying out the invention.

Prior Art Devices

Figure 1:
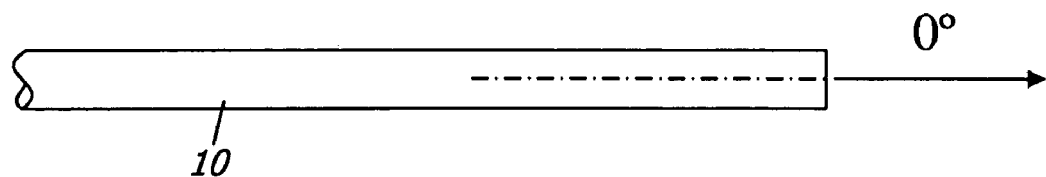
FIG. 1 schematically illustrates a series of fixed-angle endoscopes constituting a cystoscopic suite.
Figure 1:
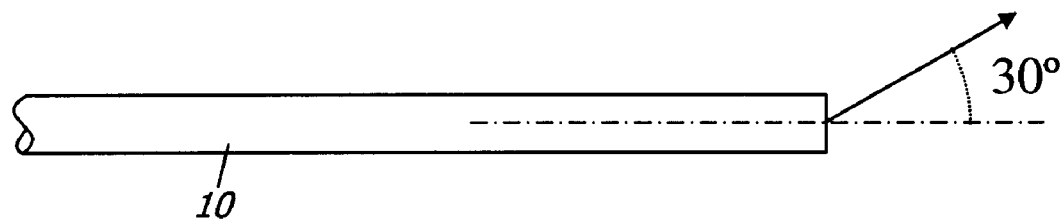
Figure 1:
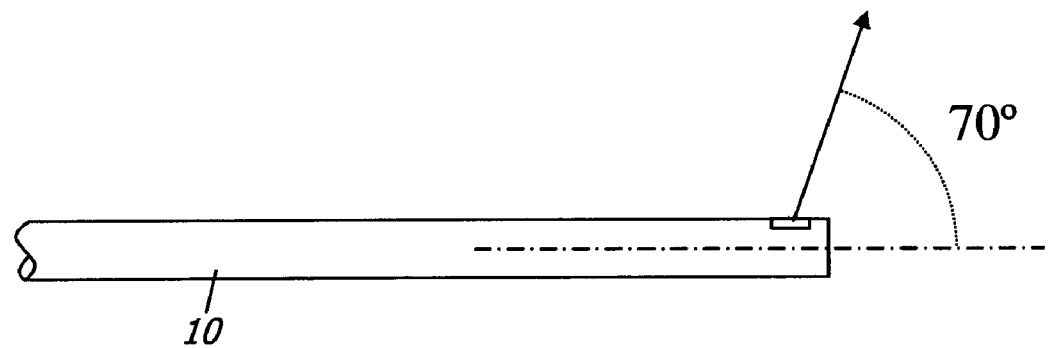
Figure 1:
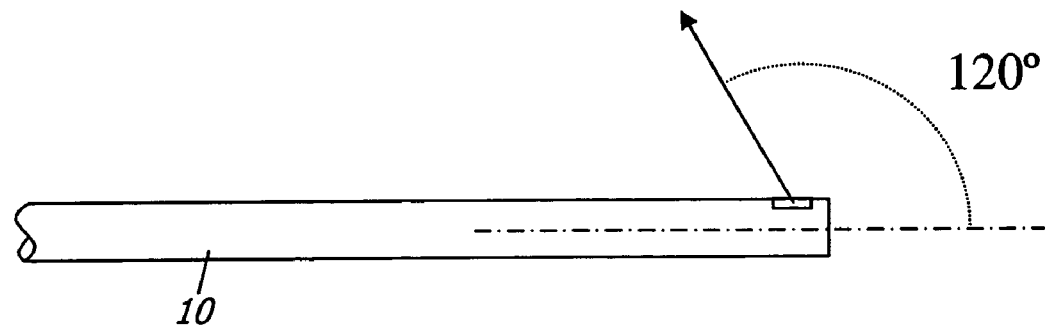

Referring now to the drawings, in which like reference numbers represent similar or identical structures throughout, FIG. 1 shows a set of fixed-angle endoscopes 10 with viewing directions of 0, 30, 70, and 120 degrees. Along with the traditional forward view, a 30 degree offset is often popular because it affords simultaneous straight forward and lateral viewing. Greater angles of 70 and 120 provide lateral and near retrospective viewing. Together these scopes 10 make up an endoscope suite as currently used in cystoscopy and neuroendoscopy. Other standard viewing angles include 12, 45, and 90 degrees.

Figure 2:
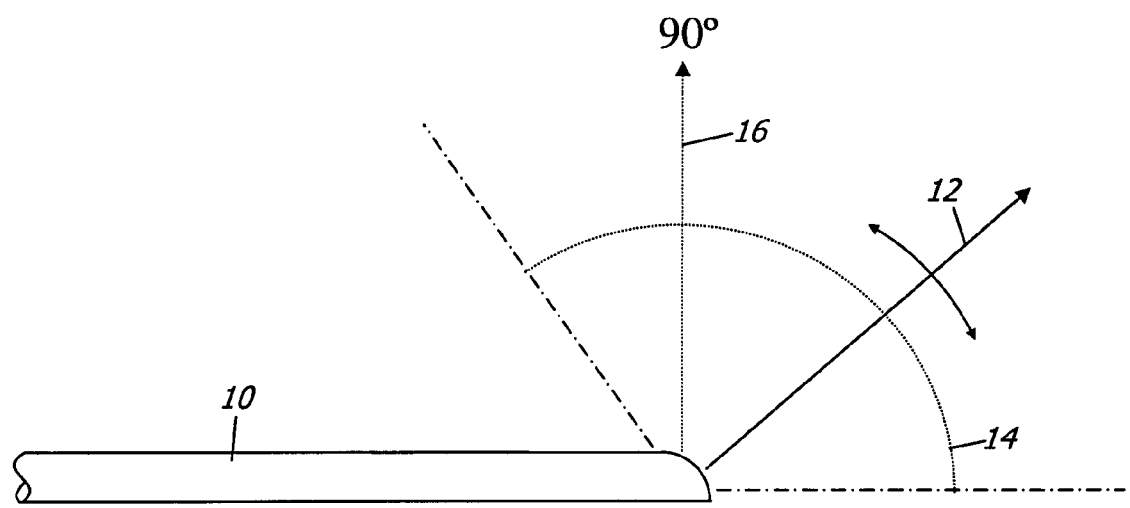
FIG. 2 shows the tip of a traditional variable direction of view endoscope.

FIG. 2 shows a common variable direction of view endoscope 10 with a view vector 12 which can swing through a range 14. The size of this range depends on the particular construction of the endoscope 10. Some variable direction of view scopes have a detent which settles the view vector 12 stably into a specific angular position 16, here 90 degrees lateral, effectively transforming the scope into a fixed off-angle scope. This detent keeps the view vector 12 from drifting away from a true 90 degree angle when the scope is manipulated. The drawback with this mechanism is that the detent cannot be repositioned if the user desires a different fixed angle, and the overall design also does not let the user reconfigure the scope 10 to add or subtract other fixed angles depending on the application.

Preferred Embodiment

Figure 3:
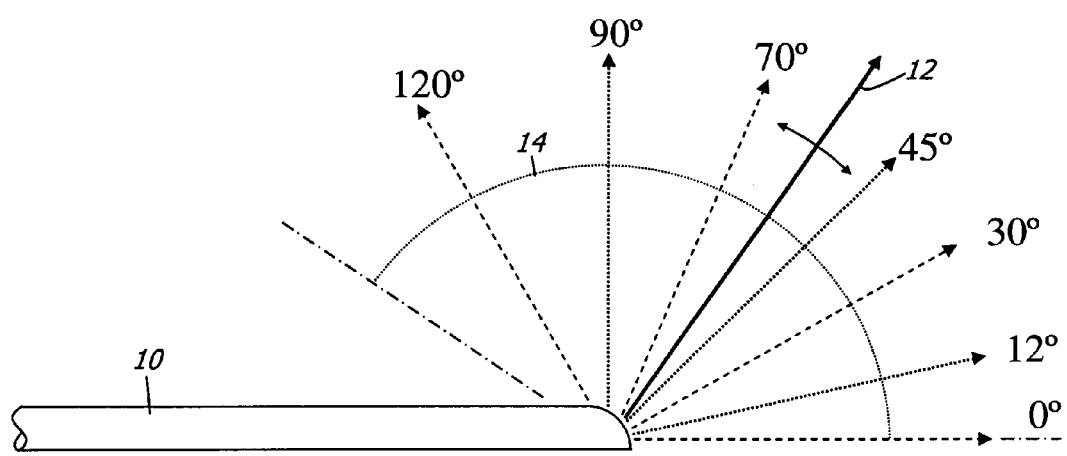
FIG. 3 shows the operation of a variable direction of view endoscope according to the preferred embodiment of the present invention.

In the preferred embodiment shown in FIG. 3, a variable direction of view endoscope 10 with a scan range 14 is configured to have its line of sight move between discrete angular positions 0, 30, 70, and 120 degrees. The scope 10 was previously configured to move between a different set of angles: 0, 12, 45, and 90 degrees. Any set of angles can be specified, and with a continuously variable viewing direction as many discrete positions as desirable can be set by the user according to the specific application or need. Depending on the construction of the endoscope 10, this can be done mechanically by adjusting a physical setting or electronically by programming the device. Mechanical configuration is accomplished with a standard transmission where a clutch can be used to shift the rotation rates, as with stick-shifted cars or revolving spindle machines like lathes or mills (The transmission and actuation techniques are not shown as there is a wealth of well known mechanisms suitable for the purpose of the present invention.). There could for example be three settings; continuous smooth motion, 30 degree increments, and 45 degree increments. Depending on the complexity of the transmission mechanism, combinations of different settings could also be possible. With an electronic or electromechanical endoscope it is possible to reconfigure the endoscope electronically (simple common support circuitry can be added if necessary). This would be done simply by programming the device, much like one would set preferences in consumer electronics, such as programming favorite radio stations or one-touch phone dialing, etc. Setting the desired angles could either be done with input buttons directly on the endoscope or it could be done through the graphical user interface (described below). Depending on the electronic configuration of the device, any number of angles can be stored, and the angles can be set to any value. The user can then rapidly switch between these preset angles without the time, thought, and effort normally required to adjust the endoscopic viewing direction. It is also possible to rapidly switch between programmed sets of preset angles, say from a standard cystoscopy set to a standard sinoscopy set. A further valuable feature is that the scope 10 can be configured so that certain button presses or double clicks take the view vector 12 to a preset home position and bypass intervening angles for rapid toggle between home and a desired viewing angle (described further below). Also, if desired, the scope 10 can always be switched into continuous mode where the angle of the view vector 12 is smoothly variable.

Figure 4A:
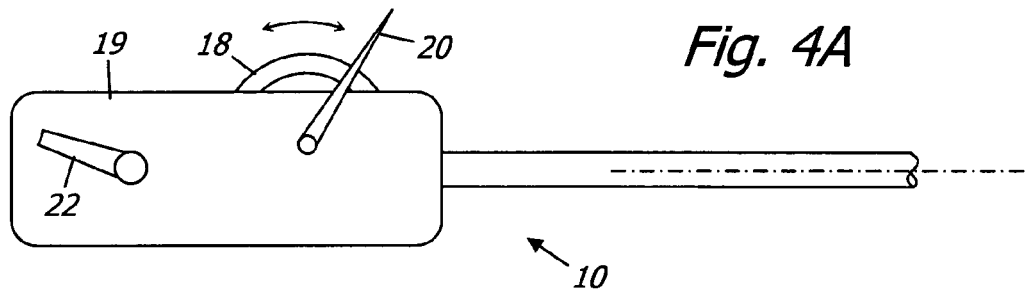
FIGS. 4A, 4B, 4C, and 4D give examples of various control interfaces according to the present invention.
Figure 4B:
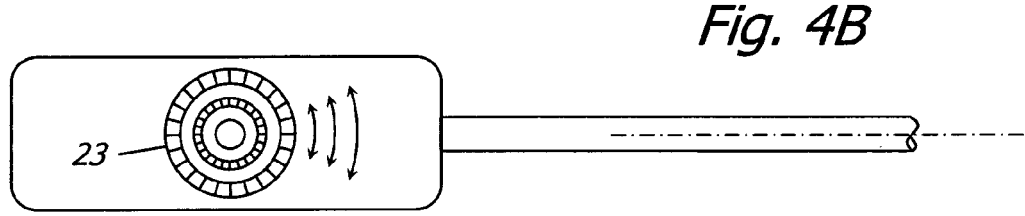
Figure 4C:
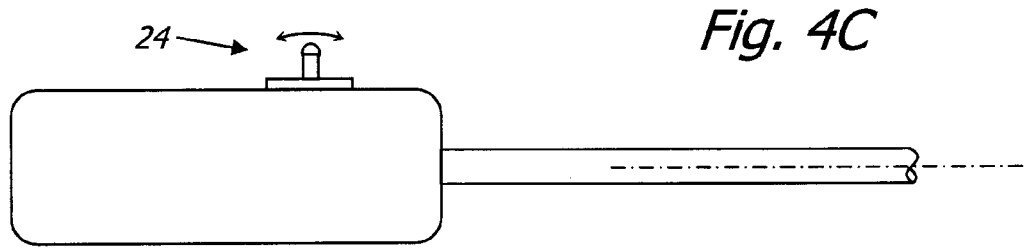
Figure 4D:
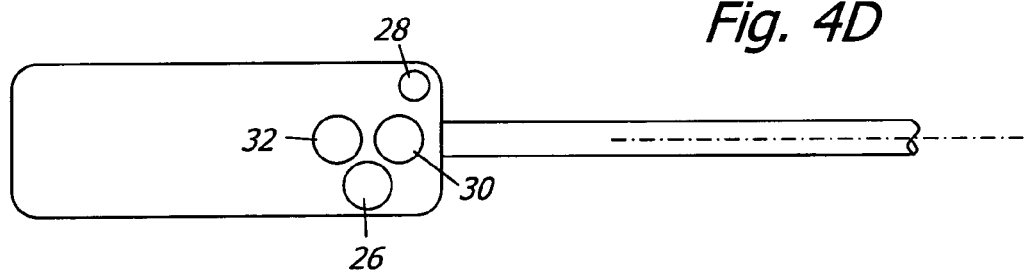

Once configured, a series of input devices can be used for controlling the endoscopic viewing direction. FIG. 4A shows a wheel 18 which can be actuated by the user's thumb (or other appropriate finger). This thumb-wheel 18, located on the endoscope handle 19, is configured to settle into discrete positions, much like a tuning knob on a digital radio. A pointer 20 could also be used. Such a pointer 20 could either serve as a control input or be passively attached to a knob or thumb-wheel 18. Aligned with the endoscopic view vector (not shown), the pointer 20 provides an important indication to the operator about where the endoscope 10 is "looking" (See U.S. Pat. No. 6,695,774 to Hale et al.). A clutch 22 is used for shifting the transmission ratio between the thumb wheel 18 and the view vector. Other mechanical input means include handles, triggers, or variable increment knobs 23, as shown in FIG. 4B. Variable increment knobs are typically found on radio tuners, oscilloscopes, and micrometers, where knobs engage different transmission ratios depending on axial position, or where there are several coaxial knobs which each engage a different setting. For an electronic or electromechanical endoscope, the input device is a joystick 24 or similar electronic switch/button, shown in FIG. 4C. By pushing the joystick 24 forward or backward, the endoscopic view vector position is incremented or decremented to an adjacent angular configuration. Depressing the joystick 24 or moving it right or left performs additional functions, such as putting the device into set mode and adjusting settings in this mode. The device can also be configured to toggle between angular positions which are not adjacent, depending on the dynamic needs of the operator. In particular, toggling between straight forward and an off-angle is very useful. During endoscopic procedures surgeons often get disoriented and would like to be able to rapidly return the view to a home position for a reference check. The best reference view is normally straight forward as it is the one to which the surgeon can most easily relate. This type of immediate return to a home reference is not possible with current endoscopes but can be done with the present invention. Double-clicking the joystick 24 for example, causes a return to home and/or there could also be a designated home-button 26, as in the alternative button based interface shown in FIG. 4D (top view). A set-button 28 which puts the device in set mode is also included in this interface, along with forward and backward buttons 30, 32. Generally, a wide range of interface configurations are possible, as exemplified by the multitude of different available video game joysticks and keypads. Which one is used will depend on the ergonomic requirements for different users and situations.

In its preferred embodiment, the present invention includes a graphical user interface (GUI) for controlling the endoscopic viewing process. This GUI, shown in FIG. 5, comprises a main section 34 for displaying the endoscopic image 36, and a section for selecting viewing parameters 38. For example, a set of default angular settings according to surgical procedure are available, allowing the user to choose the appropriate set of angles for a given procedure. A neurosurgeon would select a neurosurgical setting which runs the scope in the default multi-mode constituting the angles 0, 30, 70, and 120 degrees. An ear-nose-throat surgeon would select a sinoscopy setting which provides default viewing angles of 0, 30, 45, 70, and 90 degrees. The GUI also allows the user to customize settings, with specific toggles between angles, and personally preferred home positions for the endoscope. It also displays the current viewing angle 40, which allows the user to run a combination of continuous mode and discrete mode: the scope can be operated with a smoothly variable viewing angle, but the user will also know the running angle and can thus manually move the scope to specific desired angles without being tied to discrete preprogrammed positions. The viewing angle can also be displayed on a small readout, display, or dial located on the endoscope itself, but this is less useful because during a procedure it is inconvenient to have to look at the endoscope to get the current viewing angle. Further features give the user the choice of enabling advanced navigation features such as gravity leveling of the endoscopic image (provided the endoscope in use is equipped with the appropriate instrumentation) and superimposition of custom or default reference coordinate systems 42.

Accordingly, the present invention provides a method and interface for providing endoscopists with the advantages of traditional fixed-angle endoscopy while avoiding the disadvantages of using multiple instruments. It also provides other advantages such as rapid toggling between views and immediate return to home reference positions.

The present invention has been described above in terms of a presently preferred embodiment so that an understanding of the present invention can be conveyed. However, many alternative designs, interfaces, configurations, and structural arrangements are possible without departing from the principle of the invention. The scope of the present invention should therefore not be limited by the embodiments illustrated, but rather it should be understood that the present invention has wide applicability with respect to multi-directional viewing instruments and their use, which can be industrial or medical. All modifications, variations, or equivalent elements and implementations that are within the scope of the appended claims should therefore be considered within the scope of the invention.

We claim:

1. A method for operating a variable direction of view endoscope, the method comprising:
   providing an endoscope with a view controlling device that moves a variable view vector of the endoscope between a plurality of discrete view vector positions relative to the endoscope;
   displaying a set of the predefined, discrete view vector positions on a user interface;
   supplying a command via the user interface that causes the view controlling device to move the view vector to a first one of the discrete view vector positions displayed on the user interface;
   supplying a command via the user interface that causes the view controlling device to move the view vector directly from the first discrete view vector position to a second one of the discrete view vector positions displayed on the user interface;
   selecting particular discrete view vector positions from among the view vector positions displayed on the user interface;
   wherein the step of selecting particular discrete view vector positions includes selecting the set of discrete view vector positions from among a plurality of predefined sets of discrete view vector positions.

2. The method of claim 1, wherein the plurality of predefined sets of discrete view vector positions correspond to a plurality of procedure types.

3. The method of claim 1, wherein the plurality of predefined sets of discrete view vector positions correspond to a plurality of users.

4. The method of claim 1, further comprising displaying a graphical representation of the current position of the view vector relative to the endoscope on the user interface.

5. The method of claim 1, further comprising displaying a number that represents the current angle between the view vector and the longitudinal axis of the endoscope on the user interface.

6. The method of claim 1, wherein the endoscope has a longitudinal axis, and the set of discrete positions displayed on the user interface includes a position in which the view vector is generally parallel to the longitudinal axis.

7. The method of claim 6, wherein the view vector is moveable to the position in which the view vector is generally parallel to the longitudinal axis directly from any other position displayed on the user interface.

8. The method of claim 7, wherein the view vector is movable to any position displayed on the user interface directly from the position in which the view vector is generally parallel to the longitudinal axis.

9. The method of claim 1, wherein the view vector can toggle between the position in which the view vector is generally parallel to the longitudinal axis and any other position displayed on the user interface.

10. The method of claim 1, wherein:
    the view vector has an attendant field of view; and
    the field of view when the view vector is in the first position overlaps the field of view when the view vector is in the second position.

11. A system for operating a variable direction of view endoscope, comprising:
    a user interface; and
    an endoscope having a variable view vector, wherein said endoscope includes a view controlling device that moves the view vector between a plurality of discrete view vector positions relative to said endoscope;
    wherein said user interface displays a set of the discrete view vector positions to a user;
    wherein the set of discrete view vector positions displayed on said user interface includes a first discrete position to which the view controlling device moves the view vector to a first discrete position in response to a first command supplied by a user via said user interface;
    wherein the set of discrete view vector positions displayed on said user interface further includes a second discrete position to which the view controlling device moves the view vector directly from the first discrete position to the second discrete position in response to a second command supplied by a user via said user interface; and
    wherein said user interface displays a plurality of set identifiers corresponding to a plurality of predefined sets of the discrete view vector positions from which a user can select the set of discrete view vector positions displayed on said user interface.

12. The system of claim 11, wherein the plurality of predefined sets of discrete view vector positions correspond to a plurality of procedure types.

13. The system of claim 11, wherein the plurality of predefined sets of discrete view vector positions correspond to a plurality of users.

14. The system of claim 11, wherein said user interface displays a graphical representation of the current position of the view vector relative to said endoscope.

15. The system of claim 11, further comprising displaying a number that represents the current angle between the view vector and the longitudinal axis of said endoscope on said user interface.

16. The system of claim 11, wherein said endoscope has a longitudinal axis, and the set of discrete positions displayed on said user interface includes a position in which the view vector is generally parallel to the longitudinal axis.

17. The system of claim 16, wherein the view vector is moveable to the position in which the view vector is generally parallel to the longitudinal axis directly from any other position displayed on the user interface.

18. The system of claim 17, wherein the view vector is moveable to any position displayed on said user interface directly from the position in which the view vector is generally parallel to the longitudinal axis.

19. The system of claim 11, wherein the view vector can toggle between the position in which the view vector is generally parallel to the longitudinal axis and any other position displayed on said user interface.

20. The system of claim 11, wherein:

the view vector has an attendant field of view; and the field of view when the view vector is in the first position overlaps the field of view when the view vector is in the second position.

* * * * *